United States Patent
Monroy-Hernández et al.

(10) Patent No.: US 12,261,976 B2
(45) Date of Patent: *Mar. 25, 2025

(54) OLFACTORY STICKERS FOR CHAT AND AR-BASED MESSAGING

(71) Applicant: Snap Inc., Santa Monica, CA (US)

(72) Inventors: Andrés Monroy-Hernández, Seattle, WA (US); Sven Kratz, Mercer Island, WA (US); Rajan Vaish, Beverly Hills, CA (US)

(73) Assignee: Snap Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/384,251

(22) Filed: Oct. 26, 2023

(65) Prior Publication Data
US 2024/0056524 A1 Feb. 15, 2024

Related U.S. Application Data

(63) Continuation of application No. 17/868,395, filed on Jul. 19, 2022, now Pat. No. 11,811,964.

(51) Int. Cl.
*H04M 1/72469* (2021.01)
*A61L 9/012* (2006.01)
(Continued)

(52) U.S. Cl.
CPC ......... *H04M 1/72469* (2021.01); *A61L 9/012* (2013.01); *G06F 3/011* (2013.01);
(Continued)

(58) Field of Classification Search
CPC ...... G06F 3/011; G06F 3/0416; G06F 3/0488; A61L 9/012; A61L 2209/11
See application file for complete search history.

(56) References Cited

U.S. PATENT DOCUMENTS

| 11,811,964 B1 | 11/2023 | Monroy-Hernández et al. |
| 2011/0226864 A1 | 9/2011 | Kim et al. |

(Continued)

FOREIGN PATENT DOCUMENTS

KR 20170108437 A 9/2017

OTHER PUBLICATIONS

International Search Report and Written Opinion for International Application No. PCT/US2023/028053, dated Nov. 6, 2023 (Jun. 11, 2023)—11 pages.

(Continued)

*Primary Examiner* — Gerald Johnson
(74) *Attorney, Agent, or Firm* — CM Law; Stephen J. Weed

(57) ABSTRACT

An olfactory sticker used in chats between electronic devices to make messaging more immersive, personalized, and authentic by integrating olfactory information with traditional text-based formats and AR messaging. Olfactory stickers are used to indicate to a recipient that a message includes olfactory information. The olfactory sticker illustrates a graphical representation of a particular scent that can be sent and received via a chat or an AR message. Olfactory stickers provide the recipient control of accessing the transmitted scent at a desired time. This is particularly useful since certain olfactory information, i.e., scents, can be very direct and intrusive. Olfactory stickers are activated (i.e., release their scent) when they are tapped or rubbed by the recipient.

20 Claims, 4 Drawing Sheets

(51) Int. Cl.
   *G06F 3/01*      (2006.01)
   *G06F 3/041*     (2006.01)
   *G06F 3/0488*    (2022.01)
   *G06T 11/00*     (2006.01)
   *H04M 1/72439*   (2021.01)

(52) U.S. Cl.
   CPC .......... *G06F 3/0416* (2013.01); *G06F 3/0488* (2013.01); *G06T 11/00* (2013.01); *H04M 1/72439* (2021.01); *A61L 2209/11* (2013.01); *G06T 2200/24* (2013.01)

(56) References Cited

U.S. PATENT DOCUMENTS

| | | |
|---|---|---|
| 2015/0083817 A1 | 3/2015 | Kim et al. |
| 2017/0076403 A1 | 3/2017 | Edwards et al. |
| 2017/0131689 A1 | 5/2017 | Chan et al. |
| 2019/0176034 A1 | 6/2019 | Flego et al. |
| 2019/0196576 A1 | 6/2019 | Saarinen et al. |
| 2020/0201438 A1* | 6/2020 | Mandeville ............. G06F 3/011 |
| 2021/0209153 A1 | 7/2021 | Zhang |
| 2021/0346562 A1 | 11/2021 | Obrist et al. |

OTHER PUBLICATIONS

Zou Shangyin et al: "Simulating Olfactory Cocktail Party Effect in VR: A Multi-odor Display Approach Based on Attention", 2022 IEEE Conference on Virtual Reality and 3D User Interfaces (VR), IEEE, Mar. 12, 2022 (Mar. 12, 2022), pp. 474-482.

* cited by examiner

OLFACTORY STICKERS FOR CHAT AND AR-BASED MESSAGING

CROSS-REFERENCE TO RELATED APPLICATIONS

This application is a Continuation of U.S. application Ser. No. 17/868,395 filed on Jul. 19, 2022, the contents of which are incorporated fully herein by reference.

TECHNICAL FIELD

The present subject matter relates to electronic device interactions such as between smart devices.

BACKGROUND

Olfactory families allow individual perfumes to be classified according to their key olfactory characteristics. The olfactory families are created either by grouping together raw materials (like flowers, woods, aromatics or citrus fruits) or by taking inspiration from traditional accords (oriental or chypre, for example).

BRIEF DESCRIPTION OF THE DRAWINGS

The drawing figures depict one or more implementations, by way of example only, not by way of limitations. In the figures, like reference numerals refer to the same or similar elements.

Features of the various implementations disclosed will be readily understood from the following detailed description, in which reference is made to the appended drawing figures. A reference numeral is used with each element in the description and throughout the several views of the drawing. When a plurality of similar elements is present, a single reference numeral may be assigned to like elements, with an added letter referring to a specific element.

Figure 1:
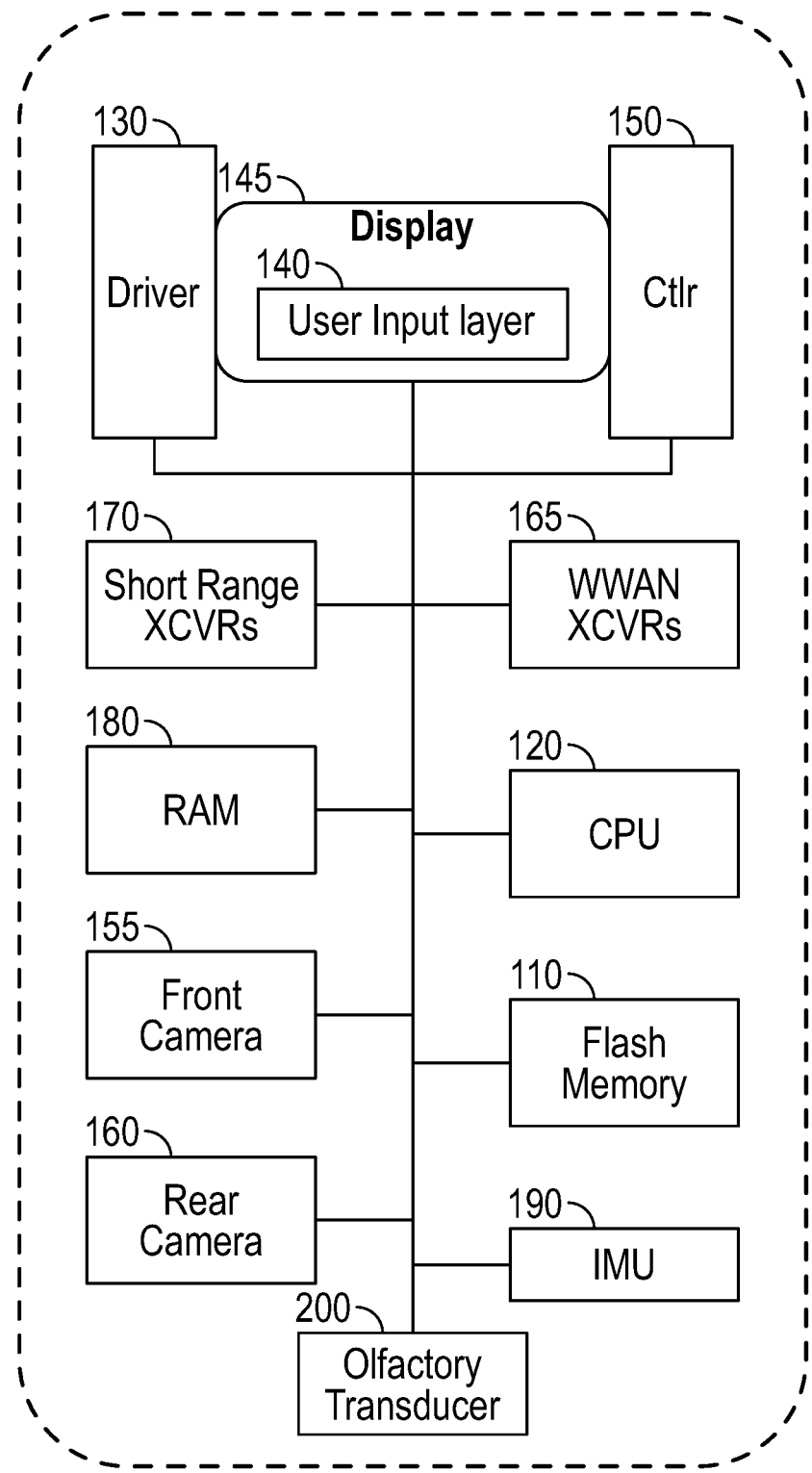
Figure 2:
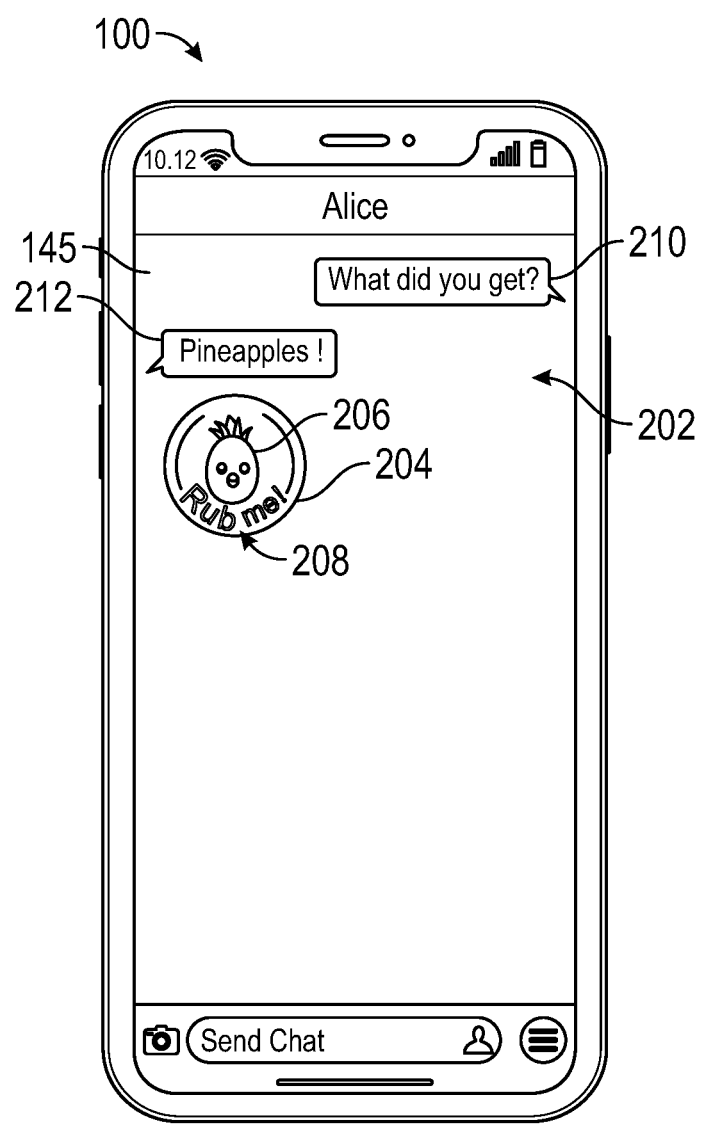
Figure 3:
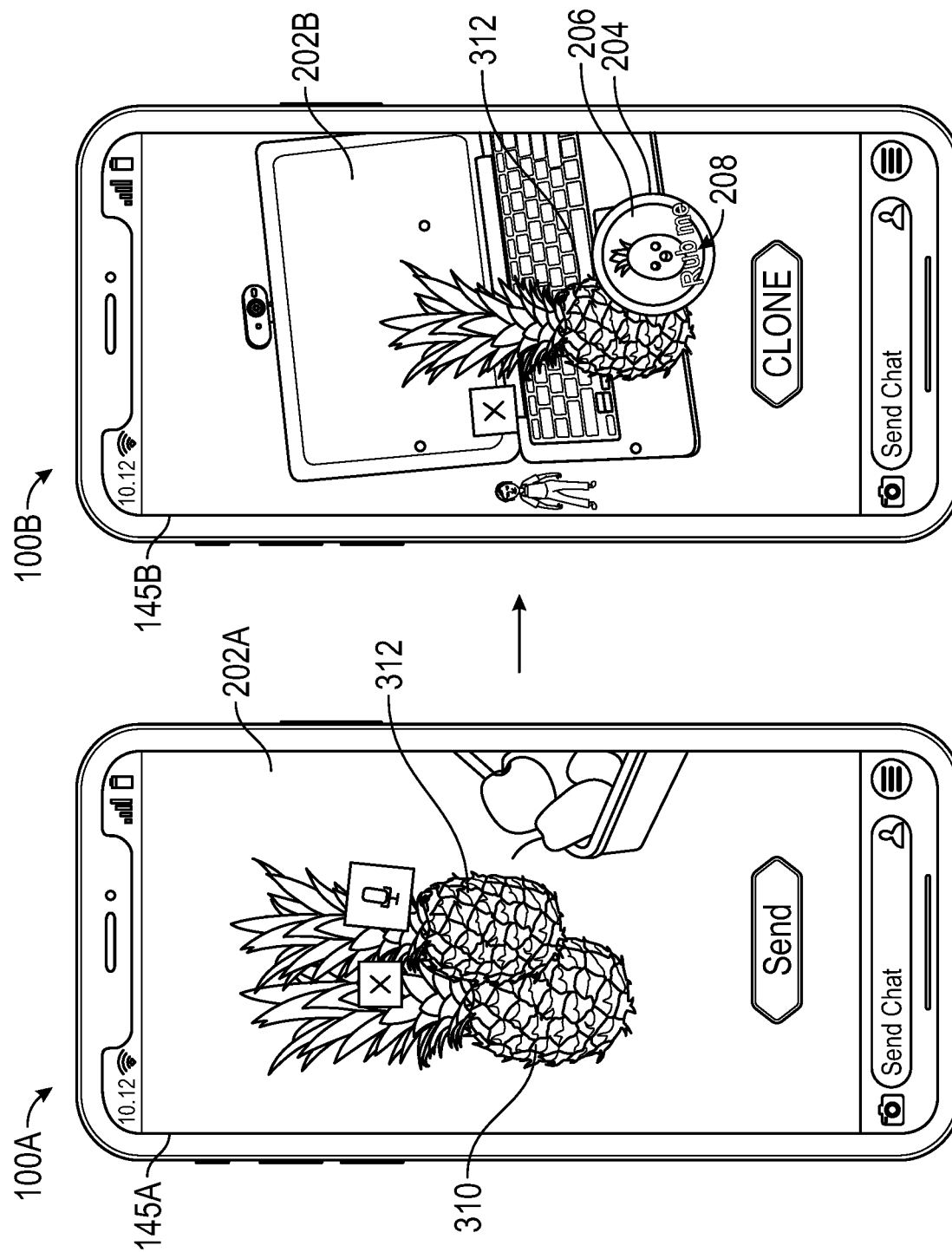
Figure 4:
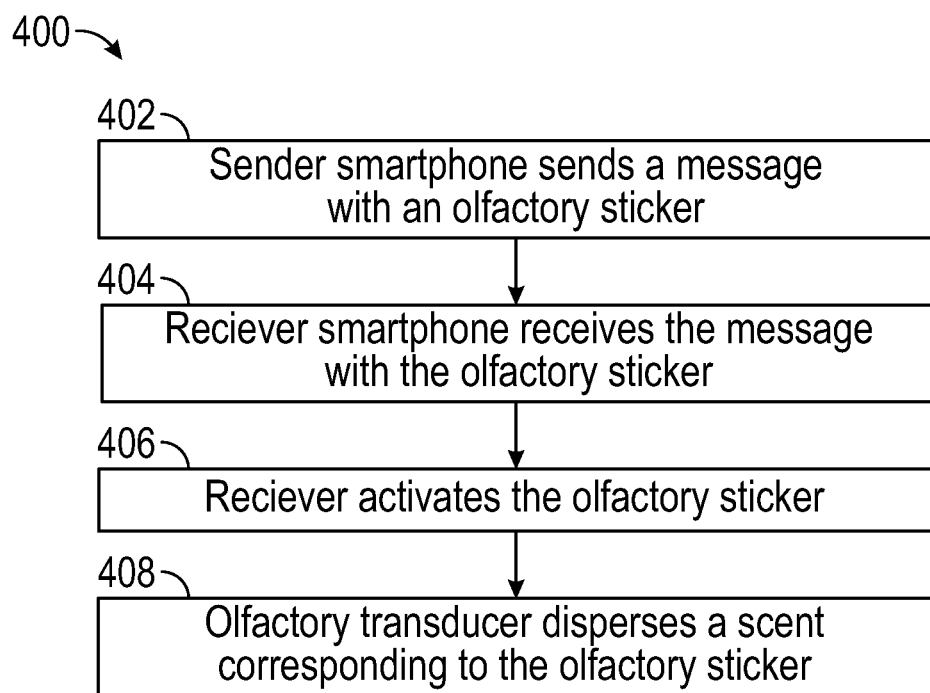

The various elements shown in the figures are not drawn to scale unless otherwise indicated. The dimensions of the various elements may be enlarged or reduced in the interest of clarity. The several figures depict one or more implementations and are presented by way of example only and should not be construed as limiting. Included in the drawing are the following figures:

FIG. 1 is a high-level functional block diagram of an example smartphone configured to receive and transmit olfactory information;

FIG. 2 is a user interface on a smartphone displaying an olfactory sticker;

FIG. 3 is an augmented reality (AR) user interface displaying an olfactory sticker; and FIG. 4 is a flowchart of a method of sending and receiving an olfactory sticker.

DETAILED DESCRIPTION

Transmission of olfactory information makes messaging between smart electronic devices more immersive, personalized, and authentic by integrating olfactory information with traditional text-based formats and AR messaging. Olfactory stickers are used to indicate to a recipient that a message includes olfactory information. The olfactory sticker illustrates a graphical representation of a particular scent that can be sent and received via a chat or an AR message. Olfactory stickers provide the recipient control of accessing the transmitted scent at a desired time. This is particularly useful since certain olfactory information, i.e., scents, can be very direct and intrusive. Olfactory stickers are activated (i.e., release their scent) when they are engaged, such as tapped or rubbed, by the recipient.

The term "connect," "connected," "couple," and "coupled" as used herein refers to any logical, optical, physical, or electrical connection, including a link or the like by which the electrical or magnetic signals produced or supplied by one system element are imparted to another coupled or connected system element. Unless described otherwise, coupled, or connected elements or devices are not necessarily directly connected to one another and may be separated by intermediate components, elements, or communication media, one or more of which may modify, manipulate, or carry the electrical signals. The term "on" means directly supported by an element or indirectly supported by the element through another element integrated into or supported by the element.

Additional objects, advantages and novel features of the examples will be set forth in part in the following description, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out herein.

Reference now is made in detail to the examples illustrated in the accompanying drawings and discussed below.

FIG. 1 illustrates a high-level functional block diagram of an example mobile device in a sample configuration. As illustrated, smartphone 100 includes a flash memory 110 that stores programming to be executed by a CPU 120 to perform all or a subset of the functions described herein. As shown in FIG. 1, the CPU 120 of the smartphone 100 includes a mobile display driver 130, a user input layer 140 (e.g., a touchscreen) of a front facing image display 145, a display controller 150, a front facing visible light camera 155, and one or more rear facing visible light cameras 160 with substantially overlapping fields of view. In such a configuration, the flash memory 110 may further include multiple images or video, which are generated via the cameras.

As shown in FIG. 1, the smartphone 100 may further include at least one digital transceiver (XCVR) 165, shown as WWAN XCVRs, for digital wireless communications via a wide-area wireless mobile communication network. The smartphone 100 also may include additional digital or analog transceivers, such as short-range transceivers (XCVRs) 170 for short-range network communication, such as via NFC, VLC, DECT, ZigBee, BLUETOOTH®, or WI-FI®. For example, short range XCVRs 170 may take the form of any available two-way wireless local area network (WLAN) transceiver of a type that is compatible with one or more standard protocols of communication implemented in wireless local area networks, such as one of the WI-FI® standards under IEEE 802.11. In certain configurations, the XCVRs 170 also may be configured to communicate with a global event database.

To generate location coordinates for positioning of the smartphone 100, smartphone 100 also may include a global positioning system (GPS) receiver. Alternatively, or additionally, the smartphone 100 can utilize either or both the short range XCVRs 170 and WWAN XCVRs 165 for generating location coordinates for positioning. For example, cellular network, WI-FI®, or BLUETOOTH® based positioning systems can generate very accurate location coordinates, particularly when used in combination.

The transceivers 165, 170 (i.e., the network communication interface) may conform to one or more of the various digital wireless communication standards utilized by modern mobile networks. Examples of WWAN transceivers 165 include (but are not limited to) transceivers configured to operate in accordance with Code Division Multiple Access (CDMA) and 3rd Generation Partnership Project (3GPP) network technologies including, for example and without limitation, 3GPP type 2 (or 3GPP2) and LTE, at times referred to as "4G," or 5G New Radio, referred to as "5G." For example, the transceivers 165, 170 provide two-way wireless communication of information including digitized audio signals, still image and video signals, web page information for display as well as web-related inputs, and various types of mobile message communications to/from the smartphone 100.

The smartphone 100 further includes a microprocessor that functions as a central processing unit (CPU) shown as CPU 120 in FIG. 1. A microprocessor is a circuit having elements structured and arranged to perform one or more processing functions, typically various data processing functions. Although discrete logic components could be used, the examples utilize components forming a programmable CPU. A microprocessor for example includes one or more integrated circuit (IC) chips incorporating the electronic elements to perform the functions of the CPU 120. The CPU 120, for example, may be based on any known or available microprocessor architecture, such as a Reduced Instruction Set Computing (RISC) using an ARM architecture, as commonly used today in mobile devices and other portable electronic devices. Of course, other arrangements of microprocessor circuitry may be used to form the CPU 120 or microprocessor hardware in a smartwatch, smartphone, laptop computer, and tablet.

The CPU 120 serves as a programmable host controller for the smartphone 100 by configuring the smartphone 100 to perform various operations in accordance with instructions or programming executable by CPU 120. For example, such operations may include various general operations of the smartphone 100, as well as operations related to the programming for applications on the smartphone 100. Although a microprocessor may be configured by use of hardwired logic, typical microprocessors in mobile devices are general processing circuits configured by execution of programming.

The smartphone 100 further includes a memory or storage system, for storing programming and data. In the example illustrated in FIG. 1, the memory system may include the flash memory 110, a random-access memory (RAM) 180, local event database, and other memory components as needed. The RAM 180 may serve as short-term storage for instructions and data being handled by the CPU 120, e.g., as a working data processing memory, while the flash memory 110 typically provides longer-term storage.

Hence, in the example of smartphone 100, the flash memory 110 is used to store programming or instructions for execution by the CPU 120. Depending on the type of device, the smartphone 100 stores and runs a mobile operating system through which specific applications are executed. Examples of mobile operating systems include Google Android, Apple iOS (for iPhone or iPad devices), Windows Mobile, Amazon Fire OS, RIM BlackBerry OS, or the like.

In sample configurations, the CPU 120 may construct a map of the environment surrounding the smartphone 100, determine a location of the smartphone 100 within the mapped environment, and determine a relative position of the smartphone 100 to one or more objects in the mapped environment. The CPU 120 may construct the map and determine location and position information using a simultaneous localization and mapping (SLAM) algorithm applied to data received from one or more sensors.

Sensor data may include images received from cameras 155 and 160, distance(s) received from a laser range finder, position information received from a GPS unit, motion and acceleration data received from an inertial measurement unit (IMU) 190, or a combination of data from such sensors, or from other sensors that provide data useful in determining positional information. In the context of augmented reality, a SLAM algorithm is used to construct and update a map of an environment, while simultaneously tracking and updating the location of a device (or a user) within the mapped environment. The mathematical solution can be approximated using various statistical methods, such as particle filters, Kalman filters, extended Kalman filters, and covariance intersection. In a system that includes a high-definition (HD) video camera that captures video at a high frame rate (e.g., thirty frames per second), the SLAM algorithm updates the map and the location of objects at least as frequently as the frame rate, in other words, calculating and updating the mapping and localization thirty times per second.

The smartphone 100 is configured to send messages to, and receive messages from, a remote smartphone device via the short range XCVRs 170 and the WWAN XCVRs 165. The messaging supports traditional chat-based messages, augmented reality (AR) messages, and hybrid chat-AR based messages. The smartphone 100 further includes an olfactory transducer 200 configured to store and disperse a small amount of one or more stored scents to be perceived by a user in proximity to the olfactory transducer 200. The CPU 120 is configured to send control signals to the olfactory transducer 200 to control the dispersion of the scents. In one example, the olfactory transducer 200 is built into the smartphone 100. In other examples, a separate device containing the olfactory transducer 200 is coupled to the smartphone 100, such as a cartridge coupled to the smartphone 100.

FIG. 2 illustrates a user interface 202 forming the user input layer 140 on the display 145 of the smartphone 100 and displaying an olfactory sticker 204. The user interface 202 displays messages 210, such as chats, sent by a user of the smartphone 100 via the short range XCVRs 170 and the WWAN XCVRs 165 to a remote smartphone, and messages 212 received by the smartphone 100 and viewable by the user. The user interface 202 is configured to send and receive the olfactory sticker 204 encoded with olfactory information corresponding to a particular scent. The encoded olfactory information is configured to activate the olfactory transducer 200 to release the corresponding scent when the user engages the olfactory sticker 204. The olfactory sticker 204 graphically represents the encoded olfactory information to the user of the smartphone 100. The olfactory sticker 204 comprises a visual preview 206 of the scent conveyed. In an example, the visual preview 206 can be an icon, symbol, cartoon, picture, emoji, Bitmoji®, text, or similar visual information. In the example shown in FIG. 2, the visual preview 206 is a cartoon pineapple used to represent a scent of a pineapple that has been sent to the smartphone 100. A variety of images may be used as a visual preview 206 for the olfactory sticker 204. For example, a vanilla flower may be used to represent the scent of vanilla, a chocolate cake may be used to represent a scent of chocolate, and a strawberry may be used to represent a scent of a strawberry.

The olfactory sticker 204 may also include text instructions 208 indicating how to engage and activate the olfactory sticker 204 to release the scent via the olfactory transducer 200. In the example shown in FIG. 2, the text instruction 208 is "Rub Me!" to indicate to the user that the olfactory sticker 204 displayed on user interface 202 must be rubbed to release the scent represented by the olfactory sticker 204. Other text, such as, "Tap Me!" may be used to indicate to the user that the olfactory sticker 204 must be tapped to release the scent represented by the olfactory sticker 204. The user interface 202 is configured to detect the interaction between the user and the olfactory sticker 204. The intensity of tapping or rubbing the displayed olfactory sticker 204 regulates the amount of scent released by an olfactory transducer 200 so that the user is not overwhelmed with a received scent. For example, a singular tap of the displayed olfactory sticker 204 translates to a small, predetermined amount of scent being released from the olfactory transducer 200, whereas two taps translate to twice the amount of scent being released as compared to the singular tap. In the example of rubbing the olfactory sticker 204, rubbing for 2 seconds translates to a small, predetermined amount of scent to be released, whereas 5 seconds of rubbing translates to twice the amount of scent being released as compared to the 2 seconds of rubbing. The configuration of rubbing the olfactory sticker 204 simulates similar, physical scent-base stickers that are activated by rubbing or scratching to provide an intuitive user interface.

FIG. 3 illustrates a sender smartphone 100A having a display 145A including user interface 202A and a receiver smartphone 100B having a display 145B including user interface 202B. The user interface 202A and a receiver user interface 202B are configured to display messaging such as an AR chat between the smartphones. The sender smartphone 100A is configured to display the AR chat on the user interface 202A with an image generated by the rear camera 160 of the sender smartphone 100A. As illustrated, the sender has selected an object 310, a pineapple, within the view of the rear camera 160 to create a cloned image 312 (i.e., "segmented image") of the object 310. The sender smartphone 100A includes a scent sensor or an image classification function to determine if information indicative of a scent can also be sent with the message. In the example of the pineapple image 312 being sent, information indicative of a scent of a pineapple is sent with the message in the form of the olfactory sticker 204. The sender smartphone 100A sends the cloned image 312 and the olfactory sticker 204 to the receiver smartphone 100B. The receiver smartphone 100B displays the cloned image 312 with the olfactory sticker 204 on the user interface 202B of the receiver smartphone 100B. In this example, the displayed olfactory sticker 204 partially overlaps the displayed cloned image 312. In other examples, the olfactory sticker 204 may be displayed to completely overlap the cloned image 312 or be displayed separately from the cloned image 312. In another example, the sender may choose to send only an olfactory sticker 204 without accompaniment of a cloned image. In an example where two users are in an AR chat proximate to each other, a shared, physically separate, olfactory transducer 200 may be used by both users to disperse the received scents.

The olfactory sticker 204 instructs the olfactory transducer 200 to emit the corresponding scent when the olfactory sticker 204 is engaged by a user of the receiver smartphone 100B, such as by tapping or rubbing the displayed olfactory sticker 204 as previously described in reference to FIG. 2.

In one example, the user of the sender smartphone 100A may select which olfactory sticker 204 to send from a displayed set of predefined olfactory stickers 204 that correlate to predefined scents that are stored in the memory 110 of the sender smartphone 100A. The receiver smartphone 100B has access to an identical, or a different, set of predefined olfactory stickers 204 to easily preview what particular scent has been received without activating the olfactory sticker 204. For example, an image of a pine tree corresponds to a fresh pine scent for both the user and the sender of the smartphones. The sender smartphone 100A sends an olfactory sticker 204 representing a pine tree to the receiver smartphone 100B and the receiver smartphone 100B knows from the predefined olfactory stickers 204 that a fresh pine scent olfactory sticker 204 was sent without activating the olfactory sticker 204. In another example, the user of the sender smartphone 100A may select a predetermined scent to accompany a custom olfactory sticker. For example, the user selects an image of a candle to be a visual preview 206 of the olfactory sticker 204 and selects the scent of the olfactory sticker 204 to be a citrus scent. The receiver smartphone 100B receives this custom olfactory sticker 204 and does not know the scent of the olfactory sticker 204 until the olfactory sticker 204 is activated and released by the olfactory transducer 200.

FIG. 4 is a flowchart 400 illustrating a method of sending and receiving a message including an olfactory sticker 204 between two smartphones 100.

At block 402, the user of the sender smartphone 100A creates and send a chat message with an olfactory sticker 204 to the receiver smartphone 100B. The processor 120 of the sender smartphone 100A sends the message via the short range XCVRs 170 or WWAN XCVRs 165. The message sent may be a traditional chat based message or an AR message. In one example, the sender smartphone 100A sends an olfactory sticker 204 selected from a predetermined set of olfactory stickers 204 that have a predetermined scent. In another example, the sender selects a scent to accompany the olfactory sticker 204.

At block 404, the receiver smartphone 100B receives the message forwarded from the sender smartphone 100A via respective short range XCVRs 170 or WWAN XCVRs 165. The message contains the olfactory sticker 204 with the encoded olfactory information. The receiver smartphone 100B displays the olfactory sticker 204 on the display 145B via the receiver smartphone 100B user interface 202B.

At block 406, the user of the receiver smartphone 100B activates the olfactory sticker 204 by interacting with the displayed olfactory sticker 204. For example, the user taps or rubs the displayed olfactory sticker 204. The user can determine the intensity of the released scent by controlling the intensity of the interaction with the displayed olfactory sticker 204.

At block 408, the processor 120 of the receiver smartphone 100B sends a signal to the olfactory transducer 200 to release a scent corresponding to the encoded olfactory information in the olfactory sticker 204 and the intensity of the user interaction with the olfactory sticker 204. The user of the receiver smartphone 100B is then able to perceive the released scent.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An electronic device, comprising:
   a processor;
   a display configured to display an image as an olfactory sticker; and
   an olfactory transducer coupled to the processor and configured to release a scent when a user interacts with the olfactory sticker, wherein the display comprises a touchscreen that is operable as a user interface and an intensity of the scent corresponds to a physical intensity of a user's interaction with the touchscreen.

2. The electronic device of claim 1, wherein the olfactory sticker is indicative of the scent.

3. The electronic device of claim 1, further comprising a transceiver coupled to the processor and configured to receive a message from a remote electronic device, the message comprising the image and information representative of the scent.

4. The electronic device of claim 1, wherein the touchscreen is configured to respond to tapping by the user on the olfactory sticker displayed on the touchscreen.

5. An electronic device, comprising:
   a processor;
   a display configured to display an image as an olfactory sticker; and
   an olfactory transducer coupled to the processor and configured to release a scent when a user interacts with the olfactory sticker, wherein the display comprises a touchscreen that is operable as a user interface and an intensity of the scent corresponds to a duration time a user rubs the olfactory sticker displayed on the display.

6. The electronic device of claim 1, wherein the image is configured to be selected from a predefined set of images.

7. An electronic device, comprising:
   a processor;
   a display configured to display an image of an olfactory sticker; and
   an olfactory transducer coupled to the processor and configured to release a scent when a user interacts with the olfactory sticker, wherein the display is operable as a user interface and an intensity of the scent corresponds to a user tapping the display.

8. The electronic device of claim 7, wherein the olfactory sticker is indicative of the scent.

9. The electronic device of claim 7, further comprising a transceiver coupled to the processor and configured to receive a message from a remote electronic device, the message comprising the image and information representative of the scent.

10. The electronic device of claim 9, wherein the display comprises a touchscreen.

11. A method of releasing a scent using an electronic device comprising a processor, a display configured to display an image of an olfactory sticker, and an olfactory transducer coupled to the processor, the olfactory transducer configured to release the scent, wherein the display comprises a touchscreen that is operable as a user interface, the method comprising:
    displaying, by the processor, the image on the display as the olfactory sticker;
    enabling, by the processor, a user to interact with the olfactory sticker; and
    releasing the scent from the olfactory transducer in response to the user interacting with the olfactory sticker at an intensity corresponding to a physical intensity of a user's interaction with the touchscreen.

12. The method of claim 11, wherein the olfactory sticker is indicative of the scent.

13. The method of claim 11, wherein the electronic device further comprises a transceiver coupled to the processor and configured to receive a message from a remote electronic device, the message comprising the image and information representative of a scent, further comprising receiving, by the processor, the image and the information representative of the scent.

14. The method of claim 11, wherein the touchscreen responds to tapping by the user on the olfactory sticker displayed on the touchscreen.

15. A method of releasing a scent using an electronic device comprising a processor, a display configured to display an image of an olfactory sticker, and an olfactory transducer coupled to the processor, the olfactory transducer configured to release the scent, wherein the display comprises a touchscreen that is operable as a user interface, the method comprising:
    displaying, by the processor, the image on the display as the olfactory sticker;
    enabling, by the processor, a user to interact with the olfactory sticker; and
    releasing the scent from the olfactory transducer in response to the user rubbing the olfactory sticker displayed on the display.

16. The method of claim 11, wherein the olfactory sticker is configured to be displayed in augmented reality.

17. A method of releasing a scent with an electronic device comprising a processor, a display configured to display an image as an olfactory sticker, and an olfactory transducer coupled to the processor, the olfactory transducer configured to release the scent, the method comprising:
   displaying, by the processor, the image on the display as the olfactory sticker;
   enabling, by the processor, a user to interact with the olfactory sticker; and
   releasing the scent from the olfactory transducer in response to the user interacting with the olfactory sticker, wherein the display operates as a user interface and an intensity of the scent corresponds to a user tapping the display.

18. The method of claim 17, wherein a message is sent in a shared augmented reality session with a remote electronic device.

19. A non-transitory computer-readable medium storing program code which, when executed, is operative to cause an electronic processor of an electronic device comprising a display configured to display an image as an olfactory sticker, and an olfactory transducer coupled to the electronic processor, wherein the display comprises a touchscreen that is operable as a user interface and an intensity of a scent corresponds to an intensity of a user's interaction with the touchscreen, to:
   display the image on the display as the olfactory sticker;
   detect a user interacting with the olfactory sticker; and
   send a control signal to the olfactory transducer to release the scent in response to detecting the user physically interacting with the olfactory sticker.

20. The non-transitory computer-readable medium storing program code of claim 19, wherein the image is indicative of the scent.

* * * * *